United States Patent [19]

Nalle, Jr.

[11] 4,353,956

[45] Oct. 12, 1982

[54] HELICAL NET

[76] Inventor: George S. Nalle, Jr., 401 Inwood Rd., Austin, Tex. 78746

[21] Appl. No.: 270,659

[22] Filed: Jun. 5, 1981

[51] Int. Cl.³ .......................... B32B 5/02; B32B 7/10; D03D 9/00

[52] U.S. Cl. .................... 428/255; 264/DIG. 81; 428/296; 428/371

[58] Field of Search ............... 264/DIG. 81; 428/255, 428/296, 371

[56] References Cited

U.S. PATENT DOCUMENTS

| | | |
|---|---|---|
| 3,123,512 | 3/1964 | Mercer . |
| 3,135,646 | 6/1964 | Hayden .............................. 428/371 |
| 3,663,352 | 5/1972 | Self et al. ............................ 428/371 |
| 3,686,380 | 8/1972 | Fairbanks .................. 264/DIG. 81 |
| 3,744,529 | 7/1973 | Jorda et al. ......................... 428/255 |
| 3,968,621 | 7/1976 | Poupitch .................... 264/DIG. 81 |
| 4,174,416 | 11/1979 | Mercer ....................... 264/DIG. 81 |
| 4,254,181 | 3/1981 | Bromley et al. ..................... 428/371 |

FOREIGN PATENT DOCUMENTS 496649  5/1978  Australia ............................. 428/255

Primary Examiner—James C. Cannon
Attorney, Agent, or Firm—C. Lamont Whitham

[57] ABSTRACT

A plastic net with a partial to a multiplicity of spirals between the interstices or crossings of the net filaments is disclosed.

9 Claims, 5 Drawing Figures

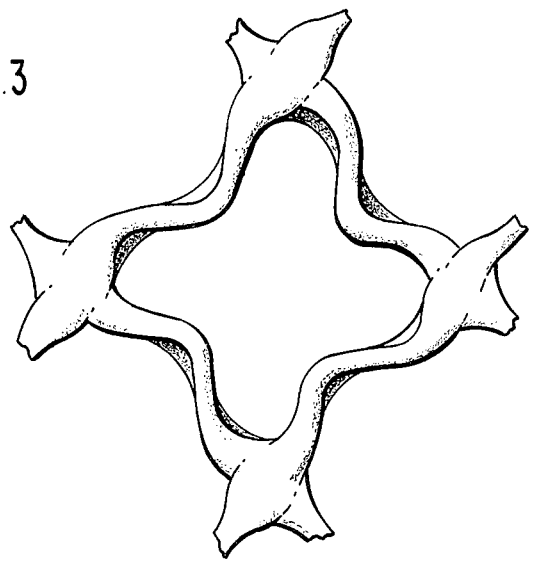
FIG.3
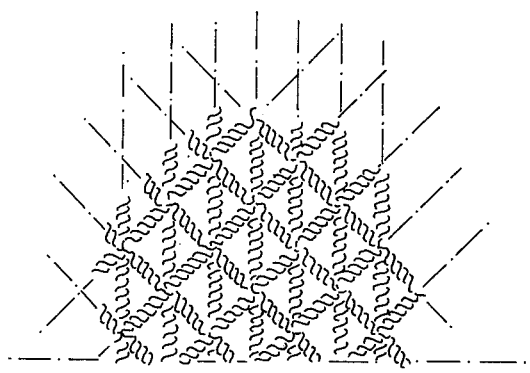
FIG.4
FIG.5
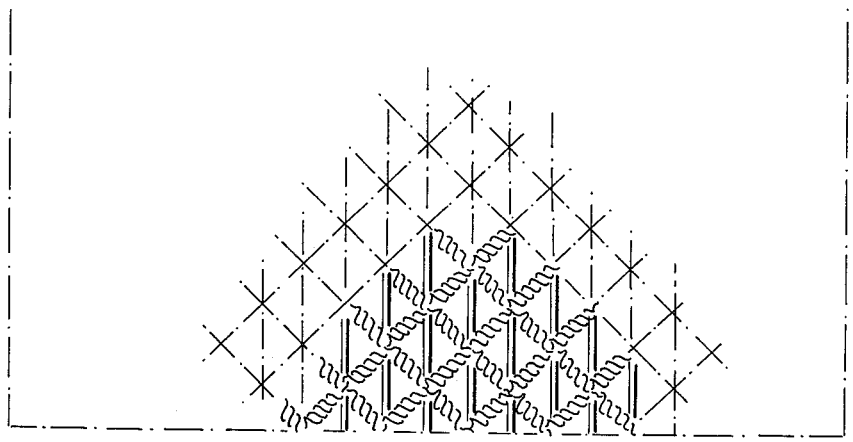

HELICAL NET

BACKGROUND OF THE INVENTION

The present invention relates to net-like structures, and more particularly to a plastic net with a partial to a multiplicity of spirals between interstices or crossings of the net filaments.

It is known to extrude plastic nets by means of relatively rotating or reciprocating die members. These die members are provided with a plurality of orifices from which the filaments of the net are extruded. When the orifices of one die are immediately adjacent the orifices of the other die, the filaments from the two dies are fused together to form the interstices or crossings of the plastic net. If only two dies are used, a two-layer net will be produced. However, it is also known as shown in U.S. Pat. No. 3,227,124 to Anderson et al, for example, to provide a die head capable of producing a three-layer net. See also U.S. Pat. No. 3,123,512. The plastic nets produced in this manner have many and diverse applications from produce bags and other packaging applications to netting for protecting agricultural crops from birds.

SUMMARY OF THE INVENTION

It is an object of the present invention to provide a new net-like structure.

It is a more specific object of this invention to provide a plastic net with a partial to a multiplicity of spirals between interstices or crossings of the net filaments.

The foregoing and other objects are embodied in a net-like structure according to the invention comprising at least two crossing layers, the first layer being a plurality of first helical filaments the axes of which are parallel and the second layer being a plurality of second helical filaments the axes of which are parallel but intersect the axes of said first helical filaments. The first and second helical filaments are fused together at each point of intersection.

The invention has several applications. For example, as a light-weight structure stretchable with low force, the invention is usable in bandages or other gauze-like applications. In heavy-weight rigid or semi-rigid structures, the invention is usable as door mats, saddle blankets, under rug padding, ventilation spacers, among other applications.

BRIEF DESCRIPTION OF THE DRAWING

The specific nature of the invention, as well as other objects, aspects, uses and advantages thereof, will clearly appear from the following description and from the drawing, in which:

FIG. 3 is a broken-away enlarged portion of the net-like structure of FIG. 1 showing in detail a partial spiral between interstices or crossings of the filaments;

FIG. 4 is a plan view illustrating a three-layer net like structure according to the invention; and FIG. 5 is a plan view illustrating another embodiment of a three-layer net-like structure according to the invention.

DETAILED DESCRIPTION OF THE INVENTION

Figure 1:
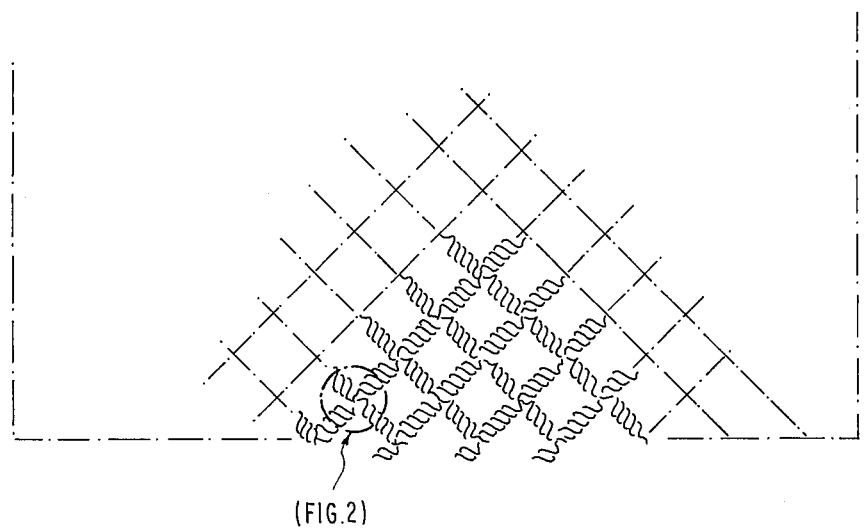
FIG. 1 is a plan view illustrating a two-layer net-like structure according to the invention.

As shown in FIG. 1 of the drawings, the net-like structure of the invention may be formed of two crossing layers. Each layer is composed of a plurality of helical filaments the axes of which are parallel, but the axes of one layer intersect the axes of the other layer. The filaments of the first layer are fused to the filaments of the second layer where they intersect.

Figure 2:
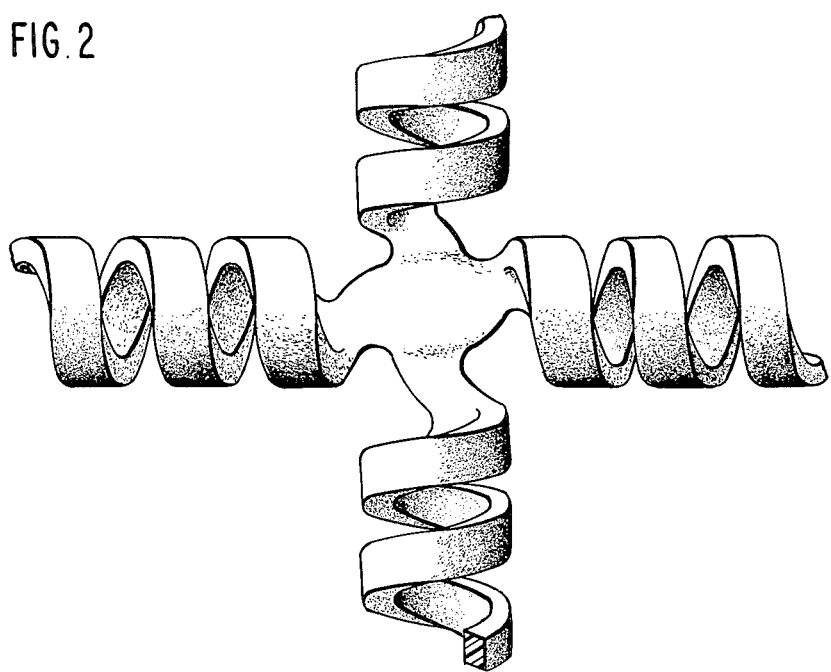
FIG. 2 is a broken-away enlarged portion of the net-like structure of FIG. 1 showing in detail a multiplicity of spirals between interstices or crossings of the filaments.

To make the net-like structure shown in FIG. 1 of the drawings, conventional net making equipment is used with the modification that each orifice of both relatively rotating or reciprocating dies is fed with two different plastic materials characterized by having different properties of contraction and orientation. One material may be a synthetic elastomeric rubber-like material, such as butyl rubber, and the other a plastic material, such as polypropylene or polyethylene. These materials are characterized by having different properties of contraction and orientation. The net is extruded from the die head in the usual manner, and then the filaments are oriented, as by stretching, well below the melt temperature of the materials, and then releasing. This causes the filaments to contract into helices. The number of helical revolutions or spirals between interstices or crossings may vary from a multiplicity of revolutions as shown in FIG. 2 to only a partial revolution as shown in FIG. 3. This is controlled by the choice of spacing between interstices and the choice and proportions of materials.

As shown in FIG. 4 of the drawings, the net-like structure of the invention may also be formed of three crossing layers. This can be accomplished with a die head of the type shown in the aforementioned Anderson et al patent suitably modified so that each orifice of all three relatively rotating or reciprocating dies is fed with two different materials. The advantage of such a three-layer net is greater density in the structure.

The net shown in FIG. 1 is referred to as a symmetrical net since the filaments of the two layers form oblique and accute angles with respect to the horizontal. What FIG. 4 adds is a third layer of filaments which are perpendicular to the horizontal. These filaments are referred to as main direction filaments since they are in the main direction of extrusion. As is well known in the art, main direction filaments are produced by a stationary die, whereas symmetrical net filaments are produced by moving dies. Also, it will be recognized by those skilled in the art that the invention could be produced as a two-layer main direction net, i.e., a net having one layer of main direction filaments and a second layer of filaments at an oblique or an accute angle to the horizontal.

A variation of the net-like structure of FIG. 4 is shown in FIG. 5. In this embodiment, the main direction filaments are composed of a synthetic elastomeric rubber-like material only. Since these filaments are composed of a single material, they will not contract into helices when the material is stretched and released. Instead, the main direction filaments will recover like a rubber band, thereby pulling the helical filaments of the other two layers closer together and giving a crepe effect to the structure.

I claim:

1. A net-like structure comprising at least two crossing layers, the first of said layers being a plurality of first helical filaments the axes of which are parallel and the second of said layers being a plurality of second helical filaments the axes of which are parallel but intersect the axes of said first helical filaments, said first and second helical filaments being fused together at each point of intersection.

2. A net-like structure as recited in claim 1 wherein there is at least a partial revolution of said first and second helical filaments between each point of intersection.

3. A net-like structure as recited in claim 1 wherein there are a multiplicity of revolutions of said first and second helical filaments between each point of intersection.

4. A net-like structure as recited in claim 1 wherein each filament is composed of two different plastic materials characterized by having different properties of contraction and orientation.

5. A net-like structure as recited in claim 4 wherein the two materials are a synthetic elastomeric rubber-like material and a plastic.

6. A net-like structure as recited in claim 4 wherein one material is a synthetic elastomeric rubber-like material and the other is a plastic material selected from the group consisting of polypropylene and polyethylene.

7. A net-like structure as recited in claim 1 comprising three crossing layers, one of said layers being composed of main direction filaments.

8. A net-like structure as recited in claim 7 wherein said main direction filaments are helical.

9. A net-like structure as recited in claim 7 wherein said main direction filaments are composed solely of a synthetic elastomeric rubber-like material.

* * * * *